United States Patent
Tahmasebi Maraghoosh et al.

(10) Patent No.: US 11,166,697 B2
(45) Date of Patent: Nov. 9, 2021

(54) SYSTEMS FOR MEASURING FORCE AND TORQUE ON ULTRASOUND PROBE DURING IMAGING THROUGH STRAIN MEASUREMENT

(71) Applicant: KONINKLIJKE PHILIPS N.V., Eindhoven (NL)

(72) Inventors: Amir Mohammed Tahmasebi Maraghoosh, Ridgefield, CT (US); Mahmoudreza Sharifi, Croton on Hudson, NY (US); Douglas Allen Stanton, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1252 days.

(21) Appl. No.: 14/768,071

(22) PCT Filed: Mar. 27, 2014

(86) PCT No.: PCT/IB2014/060193
§ 371 (c)(1),
(2) Date: Aug. 14, 2015

(87) PCT Pub. No.: WO2014/155322
PCT Pub. Date: Oct. 2, 2014

(65) Prior Publication Data
US 2016/0015363 A1  Jan. 21, 2016

Related U.S. Application Data

(60) Provisional application No. 61/806,584, filed on Mar. 29, 2013.

(51) Int. Cl.
*A61B 8/00* (2006.01)
*A61B 8/08* (2006.01)

(52) U.S. Cl.
CPC ......... *A61B 8/429* (2013.01); *A61B 8/5292* (2013.01); *A61B 2562/0261* (2013.01)

(58) Field of Classification Search
None
See application file for complete search history.

(56) References Cited

U.S. PATENT DOCUMENTS 6,122,538 A * 9/2000 Sliwa, Jr. ............ A61B 8/00
324/207.14
6,425,865 B1 * 7/2002 Salcudean ............ A61B 8/0875
600/111
(Continued)

FOREIGN PATENT DOCUMENTS

JP  2002159472 A  6/2002
JP  2010029906 A  2/2010

OTHER PUBLICATIONS

Chaldi, "A Removable Device for Axial Force and Orientation Measurement on Medical Ultrasound Probe", 9th International Multi-Conference on Systems, Signals and Devices (Year: 2012).*
(Continued)

*Primary Examiner* — Joanne M Hoffman (57) ABSTRACT

An ultrasound system employs an ultrasound probe (31), a strain sensor (33) and a workstation (20). The ultrasound probe (31) includes an ultrasound transducer for acquiring ultrasound images (40) of an anatomical region. The strain sensor (33) is arranged on the ultrasound probe (31) to measure a longitudinal strain applied by the anatomical region to the ultrasound probe (31) as the ultrasound transducer acquires ultrasound images (40) of the anatomical region. The strain sensor (33) encircles a longitudinal axis of the ultrasound probe (31) and is spaced from the ultrasound transducers relative to the longitudinal axis of the ultrasound probe (31). The workstation (20) reconstructs an ultrasound volume (41) from the ultrasound images (40) acquired by
(Continued)

ultrasound transducer, and responsive to the longitudinal strain measured by strain sensor (33), determines an axial force and/or 36 a bending force applied by the anatomical region to the ultrasound probe (31) as the ultrasound transducer acquires ultrasound images (40) of the anatomical region.

10 Claims, 5 Drawing Sheets (56) References Cited

U.S. PATENT DOCUMENTS

| | | | |
|---|---|---|---|
| 6,500,119 B1* | 12/2002 | West | A61B 5/0053 600/437 |
| 6,511,427 B1* | 1/2003 | Sliwa, Jr. | A61B 5/4869 600/438 |
| 6,612,992 B1* | 9/2003 | Hossack | A61B 8/12 600/467 |
| 2002/0049382 A1* | 4/2002 | Suh | A61B 5/103 600/449 |
| 2004/0254460 A1 | 12/2004 | Burcher et al. | |
| 2005/0004467 A1* | 1/2005 | Shiina | A61B 5/02007 600/449 |
| 2005/0043623 A1* | 2/2005 | Jurvelin | A61B 5/6843 600/449 |
| 2007/0021738 A1 | 1/2007 | Hasser et al. | |
| 2007/0030173 A1 | 1/2007 | Hasser et al. | |
| 2007/0032726 A1* | 2/2007 | Osaka | A61B 5/0048 600/459 |
| 2007/0167819 A1 | 7/2007 | Osborn et al. | |
| 2007/0293792 A1* | 12/2007 | Sliwa | A61B 5/11 600/587 |
| 2008/0269606 A1* | 10/2008 | Matsumura | A61B 5/0048 600/438 |
| 2008/0281202 A1* | 11/2008 | Fraser | A61B 5/6843 600/439 |
| 2010/0063401 A1 | 3/2010 | Nishina et al. | |
| 2010/0168596 A1* | 7/2010 | Jaeschke | A61B 5/02411 600/511 |
| 2011/0112405 A1* | 5/2011 | Barthe | A45D 44/005 600/459 |
| 2011/0152690 A1 | 6/2011 | Anthony et al. | |
| 2012/0083692 A1* | 4/2012 | Stoll | A61B 8/0825 600/437 |
| 2012/0165673 A1* | 6/2012 | Park | A61B 8/0825 600/443 |
| 2012/0190989 A1* | 7/2012 | Kaiser | A61B 5/0031 600/476 |
| 2012/0238875 A1 | 9/2012 | Savitsky et al. | |
| 2012/0253195 A1* | 10/2012 | Inoue | A61B 8/08 600/438 |
| 2012/0265057 A1 | 10/2012 | Nishina et al. | |
| 2013/0131499 A1* | 5/2013 | Chan | A61B 8/0841 600/424 |
| 2013/0158411 A1* | 6/2013 | Miyasaka | A61B 8/429 600/472 |
| 2014/0240713 A1* | 8/2014 | Kemp | A61B 5/7203 356/479 |
| 2016/0015363 A1 | 1/2016 | Tahmasebi Maraghoosh et al. | |
| 2017/0128041 A1 | 5/2017 | Hasser et al. | |
| 2017/0128144 A1 | 5/2017 | Hasser et al. | |

OTHER PUBLICATIONS

Mcgahan, J.P. et al. "Ultrasound probe pressure as a source of error in prostate localization for external beam radiotherapy", Int. J. Radiation Oncology Biol. Phys. vol. 60, No. 3, pp. 788-793, 2004.

* cited by examiner

SYSTEMS FOR MEASURING FORCE AND TORQUE ON ULTRASOUND PROBE DURING IMAGING THROUGH STRAIN MEASUREMENT

CROSS-REFERENCE TO PRIOR APPLICATIONS

This application is the U.S. National Phase application under 35 U.S.C. § 371 of International Application Serial No. PCT/IB2014/060193, filed on Mar. 27, 2014, which claims the benefit of U.S. Application Ser. No. 61/806,584, filed on Mar. 29, 2013. These applications are hereby incorporated by reference herein.

The present invention generally relates to freehand ultrasound imaging for medical procedures, particularly for prostate biopsy and brachytherapy procedures. The present invention specifically relates to a monitoring and control of consistent force applied through an ultrasound probe to an anatomical object, particularly the prostate.

Figure 1:
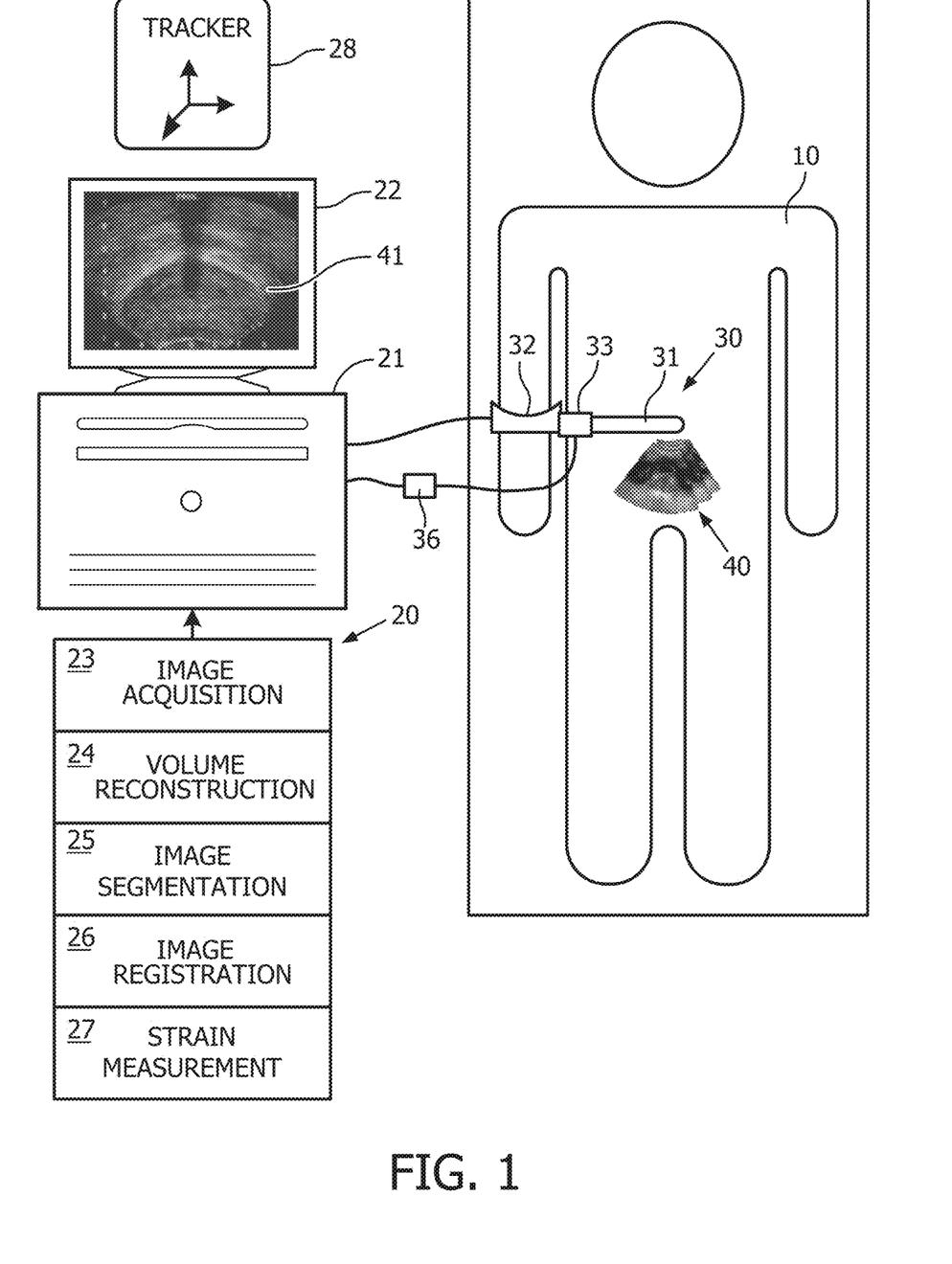
FIG. 1 illustrates an exemplary embodiment of an ultrasound system in accordance with the present invention.

Referring to FIG. 1, during a majority of ultrasound-guided biopsy and therapy procedures (e.g., prostate biopsy and brachytherapy), a whole sweep from the anatomy of interest is acquired to reconstruct a three-dimensional ("3D") volume 41 of the anatomy. Specifically, ultrasound imaging is typically carried out freehand style via a handle 32 attached to an ultrasound probe 31 having two-dimensional ("2D") ultrasound transducer(s) (not shown). An electromagnetic or optical position sensor (not shown) is attached to ultrasound probe 31 and a set of 2D B-scans 40 are acquired along with their relative coordinates in a reference coordinate system of an electromagnetic or optical tracker frame 28. The set of 2D images 40 are reconstructed into regular 3D volume 41 for visualization, guidance and analysis.

During the freehand imaging, the operator presses ultrasound probe 31 against the surface of skin or internal tissue of patient 10 while adjusting a position and an orientation of ultrasound probe 31 to find the desired image plane. During this process, the contact force between ultrasound probe 31 and the skin or tissue of patient 10 deforms the underlying tissue. For example, in transrectal ultrasound ("TRUS") imaging of the prostate, ultrasound probe 31 would be pushed against the rectum wall, which causes a significant deformation in the prostate gland. The amount of deformation correlates with the amount of applied force as well as the tissue composition.

The reconstructed image volumes 41 may be used for different applications, such as for example, anatomy segmentation 25 and multi-modality image fusion and registration 26. However, volume reconstruction 24 from freehand ultrasound probe 31 is prone to artifacts induced by the ultrasound probe pressure. Specifically, the 2D ultrasound transducer(s) of ultrasound probe 31 are required to be in close contact with the surface of the volume of interest to avoid air gaps that causes shadowing artifact in the acquired images. During a 3D sweep, the tissue being scanned is exposed to variable amount of force and each acquired 2D image 40 is captured from the tissue under different probe pressure. Therefore, the amount of pressure applied to the tissue during image acquisition by the operator may dramatically influence the quality of the acquired images 40 during the freehand style data acquisition 23. As a result, linear slice motion and nonlinear tissue deformations accumulate and produce distracting image artifacts for 3D volume 41.

Moreover, the variation in tissue geometry caused by varying contact force is the reason why ultrasound images 40 are hard to reproduce. Even if the imaging is performed on the same region of patient 10, the amount of tissue deformation certainly would be different due to changes in the force (probe pressure) and/or the biomechanical properties of the tissues.

The impact of such deformation and distortion in volume reconstruction 24 is quite dramatic in the context of automatic image segmentation 25, such as, for example, prostate gland segmentation. Furthermore, errors in image segmentation will translate into errors in registration 26 (e.g., magnetic resonance imaging to ultrasound image) and consequently will affect the biopsy and brachytherapy accuracy.

The present invention provides a force/torque management 27 for monitoring and control of consistent force applied through ultrasound probe 31 to an anatomy of interest of patient 10.

One form of the present invention is a medical instrument employing an ultrasound probe and a strain sensor. The ultrasound probe includes an ultrasound transducer for acquiring ultrasound images of an anatomical region. The strain sensor is arranged on the ultrasound probe to measure a longitudinal strain applied by the anatomical region on the ultrasound probe as the ultrasound transducer acquires images of the anatomical region. The strain sensor encircles a longitudinal axis of the ultrasound probe and is spaced from the ultrasound transducer relative to the longitudinal axis of the ultrasound probe.

A second form of the present invention is an ultrasound system employing the aforementioned medical instrument, and a workstation operable to reconstruct an ultrasound volume from the ultrasound images acquired by the ultrasound transducer(s) and responsive to the longitudinal strain measured by the strain sensor, determines an axial force and/or a bending force applied by the anatomical region to the ultrasound probe as the ultrasound transducer acquires ultrasound images of the anatomical region.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Referring to FIG. 1, an ultrasound system employs a workstation 20 having a computer 21, a monitor 22 and input devices (not shown), a bundle of software/firmware modules 23-27 and a reference tracker 28. For purposes of the present invention, computer 21 is broadly defined herein as any computer structure configured with hardware/circuitry (e.g., processor(s), memory, etc.) for processing 2D ultrasound images 40 to support medical procedures (e.g., prostate biopsy and brachytherapy procedures). To this end, modules 23-27 are programmed and installed on computer 21 to provide various functionality in support of the medical procedures.

First, an image acquisition module 23 encompasses known method(s) for receiving and storing a data set of 2D ultrasound images 40 from ultrasound probe 31 with each storage of a 2D ultrasound image 40 including a position of that image within the reference coordinate system of tracker 28 (e.g., electromagnetic or optical) via one or more sensors/markers attached to ultrasound probe 31.

Second, a volume reconstruction module 24 encompasses known method(s) for generating a 3D volume 41 from the relative positions of the 2D ultrasound images 40.

Third, an image segmentation module 25 encompasses known method(s) for partitioning the 2D ultrasound images 40 prior to reconstruction or for partitioning the 3D volume 41 into a set of disjoint segments according visual properties (e.g., grey level, texture or color) to support an easier analyze of the 3D volume 41.

Fourth, an image registration module 26 encompasses known method(s) for transforming the data set of 2D ultrasound images 40 and a data set of another imaging modality (e.g., magnetic resonance imaging or computed tomography) into one coordinate system.

Fifth, strain measurement module 27 encompasses method(s) of the present invention for determining an axial force and a bending force applied by an anatomical region of patient 10 on ultrasound probe 31 during a scanning by ultrasound probe 31 of the anatomical region (e.g., prostrate). To this end, computer 21 receives a measurement by a strain sensor 33 of a longitudinal strain applied by an anatomical region of patient 10 on ultrasound probe 31 during a scanning by ultrasound probe 31 of the anatomical region, and module 27 processes the strain measurement to determine the axial force and the bending force.

For purposes of the present invention, strain sensor 33 is broadly defined herein as any sensor structurally configured for measuring a longitudinal strain being applied by an object to an instrument, particularly for measuring a longitudinal strain being applied by an anatomical region to ultrasound probe 31 during an ultrasound scan. Also for purposes of the present invention, longitudinal strain is broadly defined herein as any strain parallel to or having a component parallel to a longitudinal axis of ultrasound probe 31.

In practice, strain sensor 33 may be arranged on ultrasound probe 31 in any manner that facilitates a measurement of a longitudinal strain being applied by an anatomical region to ultrasound probe 31 during an ultrasound scan. For example, strain sensor 33 may be adhered to or integrated with ultrasound probe 31 at or adjacent a proximal end of strain sensor 33. By further example, strain sensor 33 may be installed on a disposable casing that sits tight at or adjacent to a proximal end of ultrasound probe 31.

Also in practice, strain sensor 33 may employ one (1) or more strain gauges SG of any type (e.g., single axis, three-axial, planar, etc.) arranged on ultrasound probe 31 in manner conducive to a practical measurement of a longitudinal strain being applied by an anatomical region of patient 10 on ultrasound probe 31 during an ultrasound scan. For example, strain gauge(s) may be longitudinally arranged at or adjacent to a proximal end of ultrasound probe 31, particularly in a grid pattern for the employment of two (2) of more strain gauges. Additionally, strain sensor 33 may employ one (1) or more dummy strain gauge(s) for compensation of strain due to variation in temperature.

The following is a description of exemplary embodiment of strain sensor 33 utilized by module 27, which is followed by a description of exemplary embodiments of a scanning method and of a calibration method of the present invention implemented by module 27.

Figure 2A:
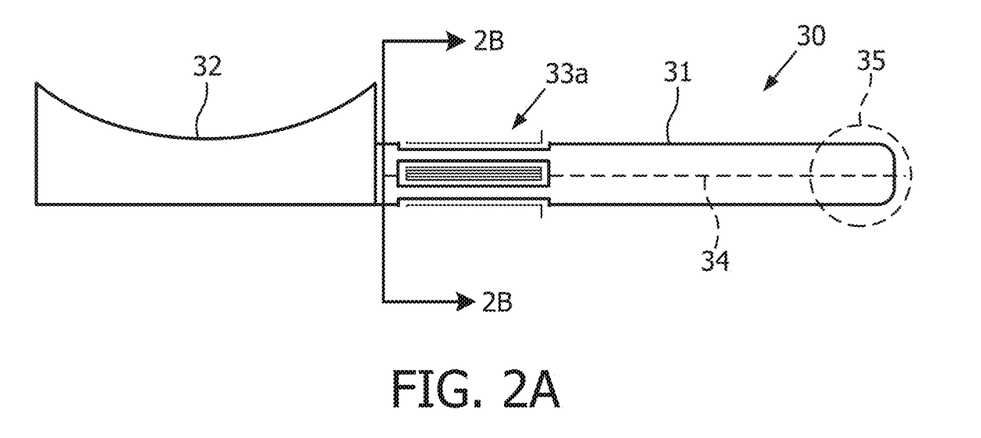
FIG. 2A illustrates an exemplary embodiment of an ultrasound probe in accordance with the present invention.

FIG. 2A shows medical instrument 30 employing ultrasound probe 31 and a handle 32 attached to proximal end of ultrasound probe 31. Ultrasound probe 31 employs an ultrasound transducer (not shown) for ultrasound imaging an anatomical region of patient 10. The ultrasound transducer is arranged at a distal end of ultrasound probe 31, typically within a dashed circle 35 in dependence upon the orientation of the ultrasound transducer relative the distal end of ultrasound probe 31.

Figure 2B:
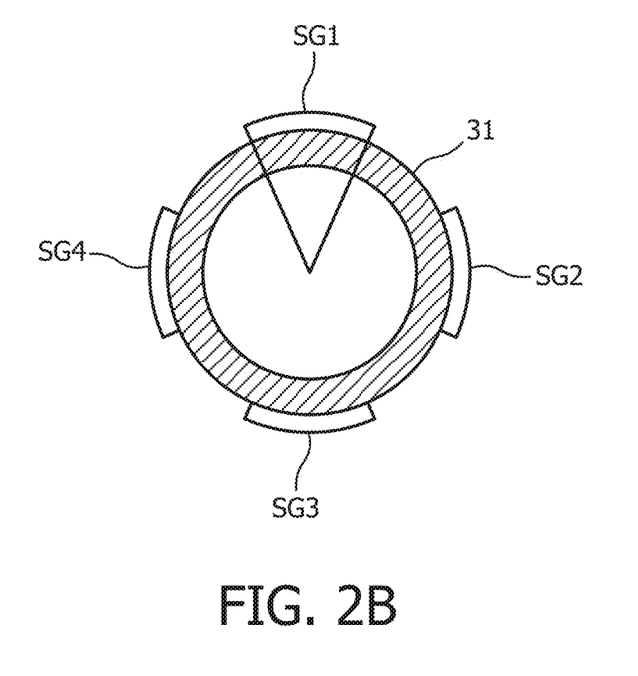
FIG. 2B illustrates a cross-sectional view of the ultrasound probe as shown in FIG. 2.

An embodiment 33a of strain sensor 33 employs four (4) strain gauges SG arranged in a grid pattern on ultrasound probe 31 arranged an equal distant from each other around the periphery of ultrasound probe 31 as shown in FIG. 2B. Strain gauges SG may consist of metallic foil that maximizes the amount of metallic wire or foil subject to strain in the parallel direction of longitudinal axis 34.

In practice, to measure small changes in resistance, strain gauges SG may be used in a bridge configuration with a voltage excitation source (not shown). Examples of the bridge configuration include, but are not limited to, a quarter-bridge configuration, a half-bridge configuration and a full-bridge configuration.

Additionally, as shown in FIG. 1, a signal conditioner 36 may be employed in view of the output voltages being relatively small. In one embodiment, signal conditioner 36 may consist of amplifiers to boost the signal level to increase measurement resolution and improve signal-to-noise ratios. Moreover, the strain gauges SG may be located in electrically noisy environments. Therefore, the signal conditioner 36 may also consist of low-pass filters to remove the high-frequency noise prevalent in most environmental settings.

The output signal(s) from signal gauges SG or alternatively signal conditioner 36 are utilized by module 27 to determine the axial force and the bending force and to display visual representation of the axial force and the bending force on the monitor 22 (e.g., a numeric and/or color coded force map overlaying volume 41). In practice, the output signal(s) from signal gauges SG may be communicated to signal conditioner 36 and/or computer 22 by any known technique and may further be communicated to computer 21 or an additional remote device for storage and display.

Figure 3A:
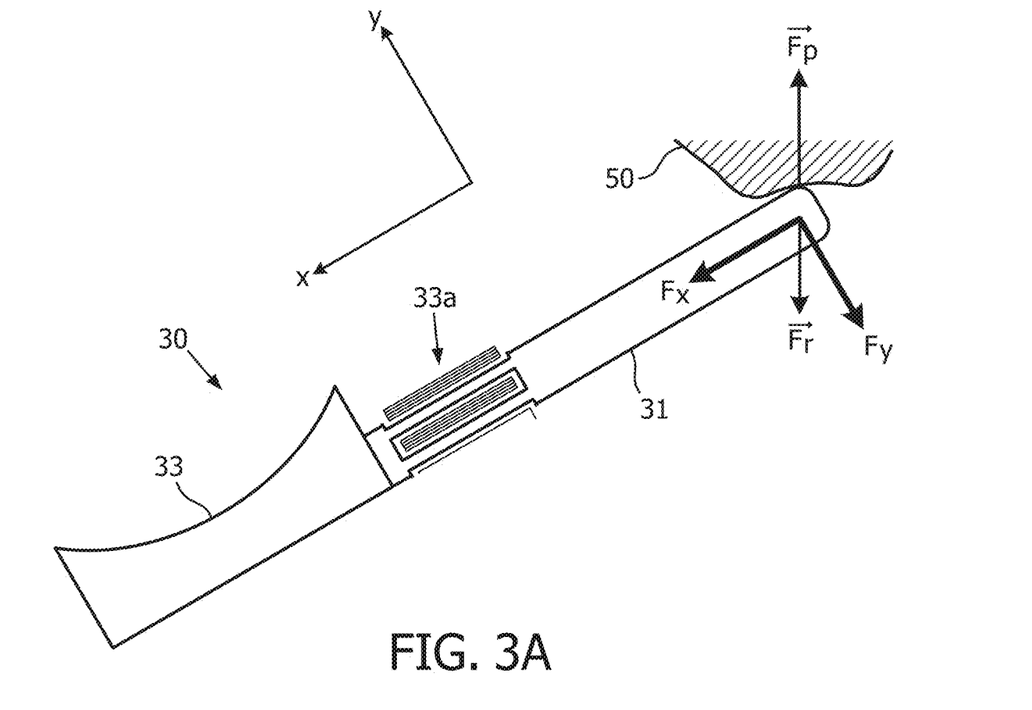
FIG. 3A illustrates exemplary forces generated during a scan of anatomical object by the ultrasound probe shown in FIG. 2A.

FIG. 3A facilitates an understanding of the axial force and the bending force applied by the anatomical region of ultrasound probe 31 during an ultrasound scan.

Specifically, referring to FIG. 3A, a probe force $F_p$ applied at the distal tip of ultrasound probe 31 to a tissue 50 (e.g., a prostrate) has the same magnitude but opposite direction of a reaction force $F_r$ from tissue 50 to ultrasound probe 31. For purposes of the present invention, reaction force $F_r$ is decomposed into two (2) components: an axial force $F_x$ and a bending force $F_y$.

Figure 3B:
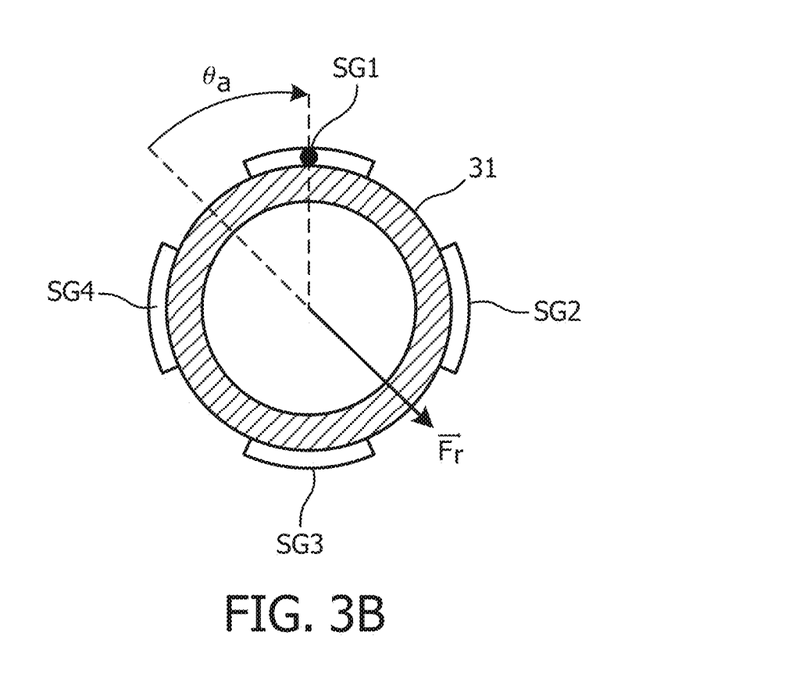
FIG. 3B illustrates a cross-sectional view of the ultrasound probe as shown in FIG. 3A.

Referring also to FIG. 3B, assuming the measured strain at points SG1, SG2, SG3 and SG4 are $\varepsilon_1$, $\varepsilon_2$, $\varepsilon_3$ and $\varepsilon_4$, respectively, axial force $F_x$ and bending force $F_y$ may be calculated from the following equations [1] and [2]:

$$F_x = -AE\left(\frac{\varepsilon_1 + \varepsilon_2 + \varepsilon_3 + \varepsilon_4}{4}\right) \quad [1]$$

$$F_y = \frac{IE}{2lr_e}\left(\sqrt{(\varepsilon_1 + \varepsilon_x)^2 + (\varepsilon_2 + \varepsilon_x)^2} + \sqrt{(\varepsilon_3 + \varepsilon_x)^2 + (\varepsilon_4 + \varepsilon_x)^2}\right) \quad [2]$$

where, $$\varepsilon_x = \frac{F_x}{AE}$$

is strain due to axial force $F_x$, E is module of elasticity of ultrasound probe 31, A is the cross-sectional area of ultrasound probe 31, l is the moment of area of ultrasound probe 31, $r_s$ is the external radius of ultrasound probe 31, and is the distance from a center each strain gauge SG to the distal tip of ultrasound probe 31. In practice, the longitudinal strain measurement is a voltage as the output of each strain gauge SG or signal conditioner 36 (FIG. 1), which is linearly related to the strain and the location of each strain gauge SG: $\varepsilon_i k_s v_i$.

Equations [1] and [2] do not depend on the rotational angle of ultrasound probe 31 around its longitudinal axis 34 since it calculates the total bending force. However, if the angle between the bending force direction and the axis of strain gauge SG1 is $\theta_a$ as shown in FIG. 3B, the angle may be calculated from the following equation [3]:

$$\theta_a = \tan^{-1}\left(\frac{\varepsilon_4 - \varepsilon_2}{\varepsilon_1 - \varepsilon_3}\right) \quad [3]$$

This angle may be used find the direction of bending force $F_y$ on a cross sectional plane of ultrasound probe 31.

Figure 4:
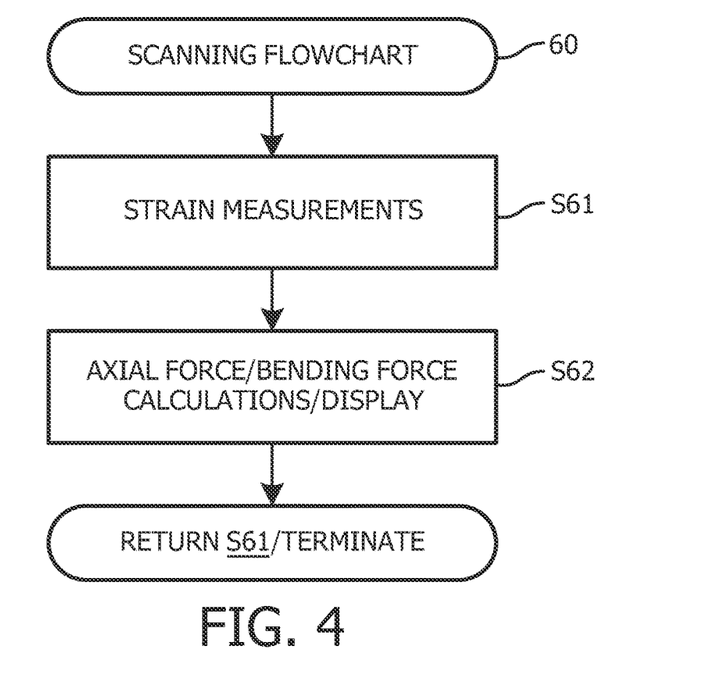
FIG. 4 illustrates a flowchart representative of an exemplary embodiment of a scanning method in accordance with the present invention.

FIG. 4 illustrates a flowchart 60 representative of a scanning method of the present invention. A stage S61 of flowchart 60 encompasses longitudinal strain measurements by strain sensor 33 (FIG. 1) as previously described herein in connection with FIGS. 2 and 3, and a stage S62 of flowchart 60 encompasses a determination by module 27 (FIG. 1) of axial force $F_x$ and bending force $F_y$ in accordance with a calculation of equations [1] and [2]. The resulting calculations may be displayed on monitor 22 (e.g., a numeric and/or color coded force map overlaying 3D volume 41). Additionally, module 27 may also calculate bending force angle $\theta_a$.

Figure 5:
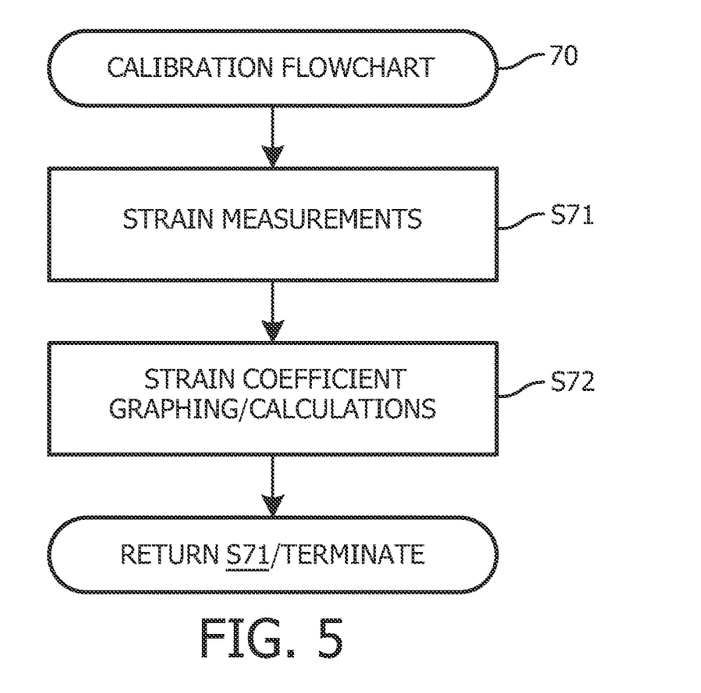
FIG. 5 illustrates a flowchart representative of an exemplary embodiment of a calibration method in accordance with the present invention.
Figure 6A:
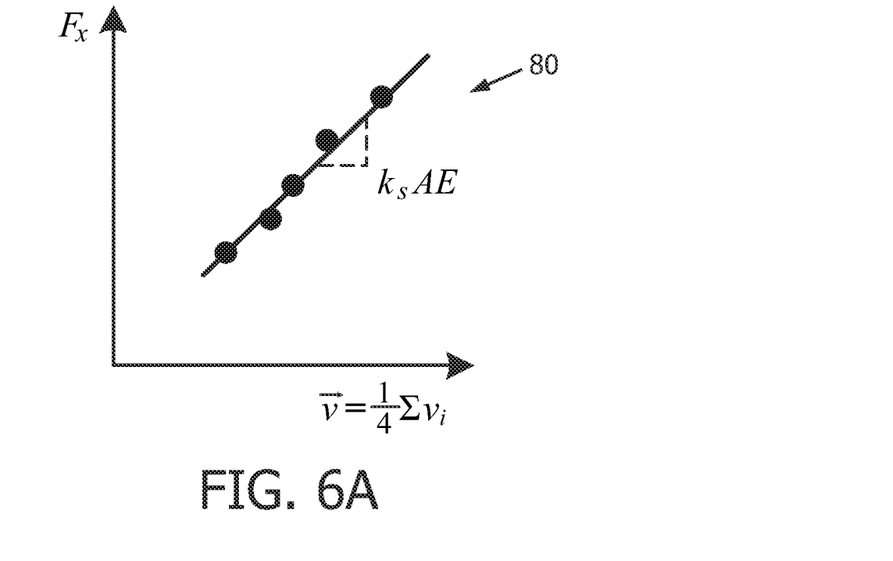
FIGS. 6A and 6B illustrate exemplary calibration graphs in accordance with the present invention.
Figure 6B:
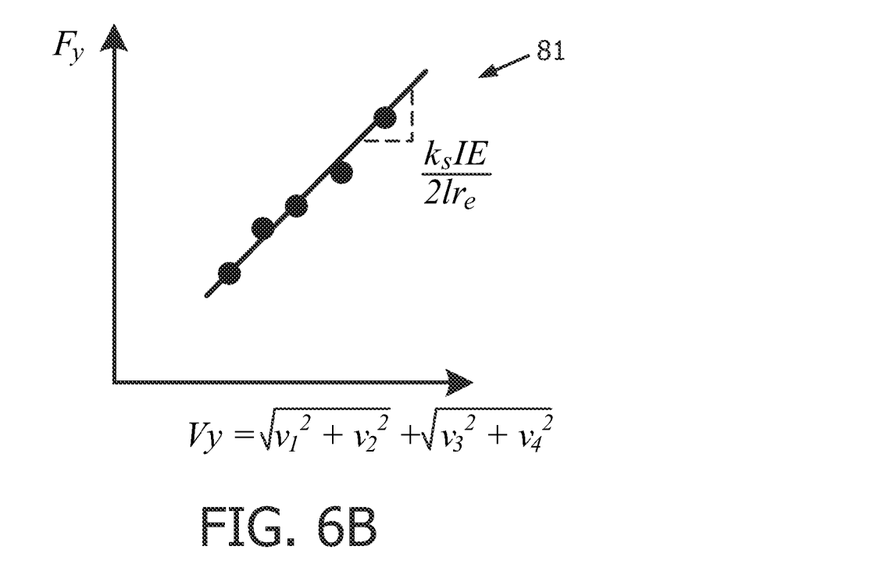

FIG. 5 illustrates a flowchart 70 representative of a calibration method of the present invention. A stage S71 of flowchart 70 encompasses strain measurements by strain sensor 33 (FIG. 1) as previously described herein in connection with FIGS. 2 and 3, and a stage S72 of flowchart 70 encompasses a calculation by module 27 of a strain coefficient $k_s$. For stage S72, the coefficient AE in the axial force equation [1] and coefficient $$\frac{IE}{2lr_e}$$

in bending force equation [2] are determined. For the calibration procedure, it is only required to know the output voltage of each strain gauge for known axial and bending forces. Since the measured voltage is linearly related to the strain, we can relate the coefficient to the measured voltage by adding additional coefficient $k_s$ as shown in respective graphs 80 (FIG. 6A) and 81 (FIG. 6B).

Referring to FIGS. 1-6B, those having ordinary skill in the art will appreciate numerous benefits of the present invention including, but not limited to, (1) a reduction in motion artifact and image distortion that is caused by uncontrolled variable force exerted by the operator during an ultrasound probe sweep of an anatomy, (2) an improvement in automatic segmentation and inter/intra modality image registration of the ultrasound images, (3) a consistent rescanning across multiple sessions by monitoring and controlling the force and the torque applied through the ultrasound probe, (4) a training tool for radiology trainees by providing live feedback on the exerted hand force to be able to learn the sufficient amount of force and torque to be applied during ultrasound scanning, (5) an estimation of the biomechanical properties of the tissue under ultrasound scanning to accurately construct a Finite Element Model (FEM) of the tissue that may be used for real-time tracking of the tissue deformation, image registration, tissue segmentation, etc., and (6) an estimation of an elasticity of tissue for calculating the stiffness or strain images of soft tissue and to detect cancerous regions which are known to have higher stiffness compared to healthy tissue.

In practice, computer 21 (FIG. 1) may provide an input mechanism for selectively enabling or disabling module 27 during an ultrasound scan.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A medical instrument, comprising:
an ultrasound probe configured to contact an anatomical region,
wherein the ultrasound probe includes an ultrasound transducer positioned at a distal end of the ultrasound probe for acquiring images of the anatomical region;
a handle attached to a proximal end of the ultrasound probe; and
a strain sensor arranged on the ultrasound probe adjacent the handle to measure a longitudinal strain applied by the anatomical region to the ultrasound probe as the ultrasound transducer contacts the anatomical region to acquire ultrasound images of the anatomical region,
wherein the longitudinal strain measured by the strain sensor represents at least one of an axial force and a bending force applied by the anatomical region to the ultrasound probe as the ultrasound transducer contacts the anatomical region, and
wherein the strain sensor includes a plurality of strain gauges arranged in a grid pattern along the ultrasound probe and encircling a longitudinal axis of the ultrasound probe.

2. The medical instrument of claim 1, wherein the plurality of strain gauges are equally spaced within the grid pattern.

3. The medical instrument of claim 1, wherein the plurality of strain gauges are one of adhered to, integrated with or installed on the proximal end of the ultrasound probe adjacent the handle.

4. An ultrasound system, comprising:
- an ultrasound probe configured to contact an anatomical region,
  - wherein the ultrasound probe includes an ultrasound transducer positioned at a distal end of the ultrasound probe for acquiring images of the anatomical region;
- a handle attached to a proximal end of the ultrasound probe;
- a strain sensor arranged on the ultrasound probe adjacent the handle to measure a longitudinal strain applied by the anatomical region to the ultrasound probe as the ultrasound transducer contacts the anatomical region to acquire ultrasound images of the anatomical region,
  - wherein the strain sensor includes a plurality of strain gauges arranged in a grid pattern along the ultrasound probe and encircling a longitudinal axis of the ultrasound probe; and
- a workstation configured to reconstruct an ultrasound volume from the ultrasound images acquired by the ultrasound transducer,
  - wherein, responsive to the longitudinal strain measured by the strain sensor, the workstation is further configured to determine at least one of an axial force and a bending force applied by the anatomical region to the ultrasound probe as the ultrasound transducer contacts the anatomical region.

5. The ultrasound system of claim 4, wherein the plurality of strain gauges are equally spaced within the grid pattern.

6. The ultrasound system of claim 4, wherein the plurality of strain gauges are one of adhered to, integrated with or installed on the proximal end of the ultrasound probe adjacent the handle.

7. The ultrasound system of claim 4, wherein the workstation determines the axial force as a function of at least one of an elasticity module of the ultrasound probe and a cross-sectional area of the ultrasound probe.

8. The ultrasound system of claim 4, wherein the workstation determines the bending force as a function of at least one of an elasticity module of the ultrasound probe, an external radius of the ultrasound probe, a moment of area of the ultrasound probe and a distance of a center of the strain sensor from a distal tip of the ultrasound probe.

9. The ultrasound system of claim 4, wherein the workstation is further configured to display visual representations for at least one of the axial force and the bending force as determined by the workstation.

10. The ultrasound system of claim 9, wherein the workstation is further configured to determine an angle between the bending force and a measuring axis of the strain sensor.

* * * * *